United States Patent
Cahan et al.

(10) Patent No.: US 11,183,276 B2
(45) Date of Patent: Nov. 23, 2021

(54) MEDICATION DISPENSER SYSTEM WITH EXACT PERSONAL DOSING

(71) Applicant: International Business Machines Corporation, Armonk, NY (US)

(72) Inventors: Amos Cahan, Dobbs Ferry, NY (US); Guy M. Cohen, Ossining, NY (US); Lior Horesh, North Salem, NY (US); Raya Horesh, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 941 days.

(21) Appl. No.: 14/979,333

(22) Filed: Dec. 22, 2015

(65) Prior Publication Data
US 2017/0172850 A1    Jun. 22, 2017

(51) Int. Cl.
*G16H 10/60* (2018.01)
*B65B 3/00* (2006.01)
*G16H 20/13* (2018.01)

(52) U.S. Cl.
CPC ............. *G16H 10/60* (2018.01); *B65B 3/003* (2013.01); *G16H 20/13* (2018.01); *B65B 2210/04* (2013.01); *B65B 2220/14* (2013.01)

(58) Field of Classification Search
CPC ............................................. G06Q 50/22–24
See application file for complete search history.

(56) References Cited

U.S. PATENT DOCUMENTS

| | | |
|---|---|---|
| 5,700,998 A * | 12/1997 | Palti .................. G16H 20/13 235/375 |
| 5,925,014 A | 7/1999 | Teeple, Jr. |
| 7,359,765 B2 | 4/2008 | Varvarelis et al. |
| 7,575,567 B2 | 8/2009 | Simpkins |
| 8,029,468 B2 | 10/2011 | Kriesel et al. |
| 8,316,798 B2 | 11/2012 | Ito |

(Continued)

OTHER PUBLICATIONS

ScriptPro. "Anatomy of a Robot". Feb. 1, 2015. Archive.org. (Year: 2015).*

(Continued)

*Primary Examiner* — Robert A Sorey
(74) *Attorney, Agent, or Firm* — Kristofer Haggerty; Michael J. Chang, LLC

(57) ABSTRACT

A medication dispenser system and use thereof for providing exact personal dosing for a patient are provided. In one aspect, a method for dispensing medications is provided. The method includes the steps of: obtaining patient information and a list of the medications for the patient; calculating a personal dose of each of the medications for the patient using the patient and cross-medication interaction information; and preparing treatments each containing the personal dose of each of the medications in a single treatment. In another aspect a system for dispensing medications includes: a patient information component for obtaining patient information and a list of the medications for the patient; a dosage calculator component for calculating a personal dose of each of the medications for the patient using the patient information; and a medication dispenser component for preparing treatments each containing the personal dose of each of the medications in a single treatment.

19 Claims, 4 Drawing Sheets

(56) References Cited

U.S. PATENT DOCUMENTS

| | | | |
|---|---|---|---|
| 2005/0210834 A1* | 9/2005 | Kamineni | A61J 1/20 53/415 |
| 2005/0218152 A1* | 10/2005 | Simon | A61J 7/0084 221/203 |
| 2006/0078897 A1* | 4/2006 | Wedinger | G16H 20/10 435/6.16 |
| 2007/0150025 A1* | 6/2007 | Dilorenzo | A61B 5/0476 607/45 |
| 2008/0190953 A1* | 8/2008 | Mallett | B07C 7/005 221/13 |
| 2008/0272138 A1* | 11/2008 | Ross | G07F 11/60 221/1 |
| 2012/0041778 A1 | 2/2012 | Kraft | |
| 2013/0149377 A1* | 6/2013 | Alfano | A61J 3/07 424/451 |
| 2015/0088304 A1 | 3/2015 | Ameye et al. | |

OTHER PUBLICATIONS

L. Hirshfield et al., "Dropwise Additive Manufacturing of Pharmaceutical Products for Solvent-Based Dosage Forms," Journal of Pharmaceutical Sciences, vol. 103, No. 2, 2014, pp. 496-506 (published Dec. 2013).

J. Wechsler, "Combination products raise manufacturing challenges," Pharmaceutical Technology, vol. 29, Mar. 2005, pp. 32-40.

\* cited by examiner

MEDICATION DISPENSER SYSTEM WITH EXACT PERSONAL DOSING

FIELD OF THE INVENTION

The present invention relates to a medication dispenser system, and more particularly, to a medication dispenser system and use thereof for providing exact personal dosing for a patient.

BACKGROUND OF THE INVENTION

The optimal dose of a medication that is administered to a patient depends on many factors that are specific to the patient characteristics. For example, levothyroxine is a replacement for a hormone normally produced by the thyroid gland. The dose of levothyroxine that a doctor prescribes depends on a variety of factors including the patient's age and body weight. The levothyroxine pill is available at doses of 25, 50, 75, 88, 100, 112, 125, 150, 175, 200 and 300 milligrams (mg). If a patient's optimal dose falls between two existing doses, the patient will be either under or over dosed. In yet another example, amoxicillin (a very common antibiotic) is only available in pills of 250, 500, and 875 mg. It would be desired for the patient to take the optimal dose for his/her condition. However, since the available pill dosages are limited to several pre-manufactured dosages most patients are either under or over dosed.

Yet another problem with medications is the chance of handling errors when multiple medications are prescribed for a condition. For instance, patients must track which medications to take, and when, and can inadvertently miss a dose by mistake. Thus, it would be desirable if a patient could take just one pill that combines all the prescribed medications. Indeed, some combinations of medications in a single pill have been introduced, but these are very limited in their active ingredient compositions and, like most other medications, are offered in fixed doses.

Further, patients who use over-the-counter (OTC) medications are even more likely to be under or over dosed since these medications in most cases are available in one strength, and lack the oversight of a prescription that is filled by a pharmacist. Dietary supplements (for example, vitamin pills) exhibit similar issues. Patients who may have a deficiency in one vitamin or mineral are usually forced to take a pill that contains the deficient vitamin but also a plethora of other vitamins and minerals.

Therefore, a means for providing patients with a correct, exact dosage of medication would be desirable.

SUMMARY OF THE INVENTION

The present invention provides a medication dispenser system and use thereof for providing exact personal dosing for a patient. In one aspect of the invention, a method for dispensing medications is provided. The method includes the steps of: obtaining patient information and a list of the medications for the patient; calculating a personal dose of each of the medications for the patient using the patient information; and preparing treatments each containing the personal dose of each of the medications in a single treatment.

In another aspect of the invention, a system for dispensing medications is provided. The system includes: a patient information component for obtaining patient information and a list of the medications for the patient; a dosage calculator component for calculating a personal dose of each of the medications for the patient using the patient information; and a medication dispenser component for preparing treatments each containing the personal dose of each of the medications in a single treatment.

A more complete understanding of the present invention, as well as further features and advantages of the present invention, will be obtained by reference to the following detailed description and drawings.

DETAILED DESCRIPTION OF PREFERRED EMBODIMENTS

As provided above, conventional treatments involving medications have the potential for a variety of errors such as under or over dosing based on factors such as, commercially-available medications are only available in fixed doses, error at the dispensary level (e.g., errors made by pharmacists when dispensing the medication) and/or at the patient level (e.g., patient mistakenly fails to take the correct dosage at the correct time), a lack of personalized guidance on taking over-the-counter (OTC) medications (i.e., since a prescription is not needed), etc. Advantageously, provided herein is a system and techniques for use thereof for dispensing personalized doses of medication for a patient such that, e.g., the patient simply has to take a single treatment (e.g., a single pill) to receive the correct dosage of one or more medications the patient is taking.

The term "medication" as used herein generally refers to any substance used by an individual by internalizing it for the purpose of improving or maintaining health, or curing or alleviating a disease or a symptom. By way of example only, this includes prescription or OTC products, supplements, natural extracts (e.g., that one might add to a drink or shake), ingestible/injectable treatments, etc. Prescription products require a doctor's prescription to be obtained, whereas OTC products, supplements, etc. do not require a doctor's prescription. When a prescription is needed, the patient may take the prescription to a pharmacy where a pharmacist provides the prescribed medication(s). The term "patient" as used herein generally refers to any person receiving the "medication" and applies to both to individuals who has a medical conditions, as well as healthy people who are interested in maintaining their wellness.

As will be described in detail below, the present medication dispenser system generally has the following beneficial features: 1. it enables the packaging of a precise dose of a medication in capsules, tablets, caplets, powder or liquid formulation (enteral or parenteral) for optimal treatment; 2. it allows for the combination of several medications into one capsule, tablet, caplet, powder or liquid formulation; 3. it calculates the optimal dose for a patient based on his/her medical records if available, and/or based on the patient's age, weight, gender, proteomic/microbiomic profiling, and other medications that he/she may be taking; 4. it enables tailoring treatment of variable doses and medication combinations for each day by packaging the medications into capsule marked with "day 1," "day 2," etc.; 5. it can be used to produce liquid meals with integrated medications at the dose required by a particular patient; 6. it encapsulates medication/nutrition in desired type of packaging appropriate to storage conditions as well as desired release mechanism (e.g., fast vs. slow release and/or enteric formulation resistant to gastric acidity).

Figure 1:
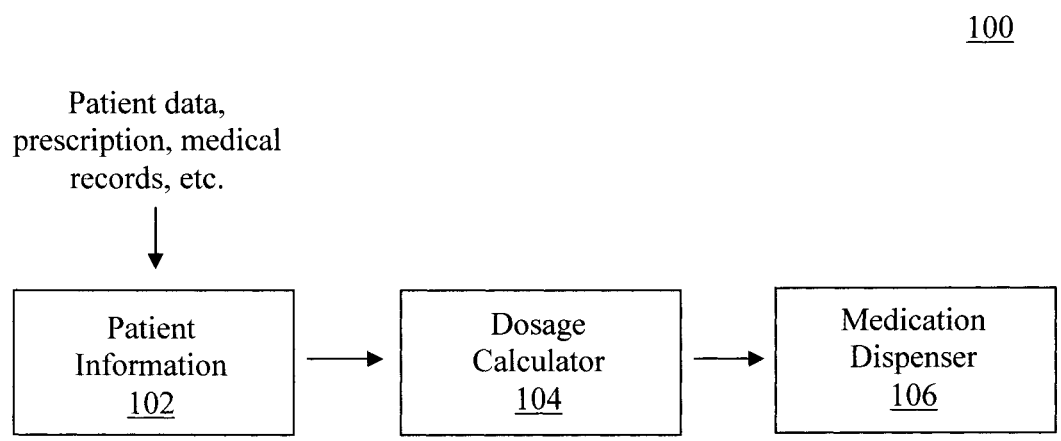
FIG. 1 is a schematic diagram illustrating a medication dispenser system according to an embodiment of the present invention.

An overview of the present medication dispenser system 100 is now described in detail by way of reference to FIG. 1. System 100 is a computerized system (such as a web-based application, an application (or app) for a mobile device, or a kiosk). According to one exemplary embodiment, the specific components (see below) of system 100 are embodied (e.g., in circuitry) within an apparatus, such as apparatus 500 described in conjunction with the description of FIG. 5, below.

As shown in FIG. 1, system 100 includes a first component 102 (labeled "Patient information") configured to obtain patient information. The patient information may be obtained from a variety of sources. By way of example only, the patient herself might simply provide the information, such as height, weight, gender, age, other medications the patient is taking, etc., directly to the system. To use a non-limiting example, the patient might access system 100 through a web-based or mobile device app through which the patient can provide such information. Additionally, system 100 may include a scale, three-dimensional (3D) scanner, and/or other means to measure relevant patient attributes (e.g., height, percentage of body fat etc.) to obtain "patient information." Stations for obtaining this patient data can be located at the patient's home (e.g., scale, blood pressure monitor, scanner, etc. connected to system 100 through phone, Internet, etc. connections) and/or at remote locations (e.g., at health care centers, clinics, hospitals, pharmacies, etc.). Suitable encryption and/or other techniques known in the art are implemented to protect the privacy of the patient.

Alternatively, the patient might authorize system 100 to retrieve the patient's medical records. Most medical records are kept in a digital form and can be retrieved by system 100, e.g., via the Internet. Authorization procedures to retrieve patients' medical records are well established in the medical field. Again, it is preferable for encryption techniques to be implemented to ensure that the patient's privacy is maintained. If system 100 has access to the patient's medical records, then the patient may not need to provide any further data (since the parameters such as height, weight, gender, other medications the patient is taking, etc.) are likely already present in the medical records).

If the medication in question is a prescription, then system 100 may also obtain patient information from the prescription itself. For instance, the doctor writing the prescription, can upload its information to system 100 (e.g., via web-based or mobile device-based app). The prescription will contain the particular medication(s) and/or a prescribed dosage. When no prescription is needed (such as in the case of OTC medications, supplements, etc.) the information provided by the patient and/or through the patient's medical records will be used by system 100.

The patient information from component 102 is then used by a second component 104 of system 100 (labeled "Dosage Calculator") to determine the exact dosage for the patient. This calculation can be based on a variety of different factors. For instance, given the scenario above where the patient has provided his/her own patient data (such as height, weight, gender, age, etc.), the dosage calculator will calculate the proper dosage for the given medication(s) based on that data. Similarly, when the patient's medical records are available this data can be used (alone or in conjunction with the data provided by the patient herself) to determine the proper dosage. It is notable that the Dosage Calculator can leverage available dosage data for the given medications. For instance, the manufacturer of a medication might publish dosage specifications for their products and the dosage calculator simply has to apply the patient's data (height, weight, etc.) to determine the proper dosage. In the same manner, the manufacturer might specify potential medication interactions that affect usage, dose, etc. This information can also be taken into account via the Dosage Calculator.

The Dosage Calculator then provides the dosage(s) of the medication(s) to a third component 106 of system 100 (labeled "Medication Dispenser"). The Medication Dispenser is configured to dispense the medications in the proper dosages. The details of the Medication Dispenser component of system 100 will be provided in detail below. In general however, the Medication Dispenser includes a controller for each medication being dispensed, such that an exact controlled amount of each medication can be dispensed—the amount being based specifically on the dosage determined by the Dosage Calculator. As will be described in detail below, the present techniques can be utilized to place the specific dosage of each of the (multiple) medications into a single delivery unit (e.g., tablet, capsule, syringe vial, etc.) such that the patient need only take one administration to receive the proper dosage of each of the (multiple) medications.

It is notable that while the various components of system 100 may be all present at a single location, this is not a requirement, and embodiments are anticipated herein involving a distributed system 100. For example, the Patient Information and Dosage Calculator may be present at one location (such as an intake center) to process incoming orders (submitted, e.g., via a web-based or mobile device-based app). The orders can be processed, including a determination of the correct dosage for each medication. That information (medication(s), dosage, etc.) can then be sent to another location that fills the order via the Medication Dispenser component. For example, the orders may be filled at a distribution center, a pharmacy, etc. Alternatively, system 100 may be embodied in its entirety at a given location, e.g., where the patient places an order, his/her information is obtained/retrieved (as described above), and the proper dosage is dispensed.

Figure 2:
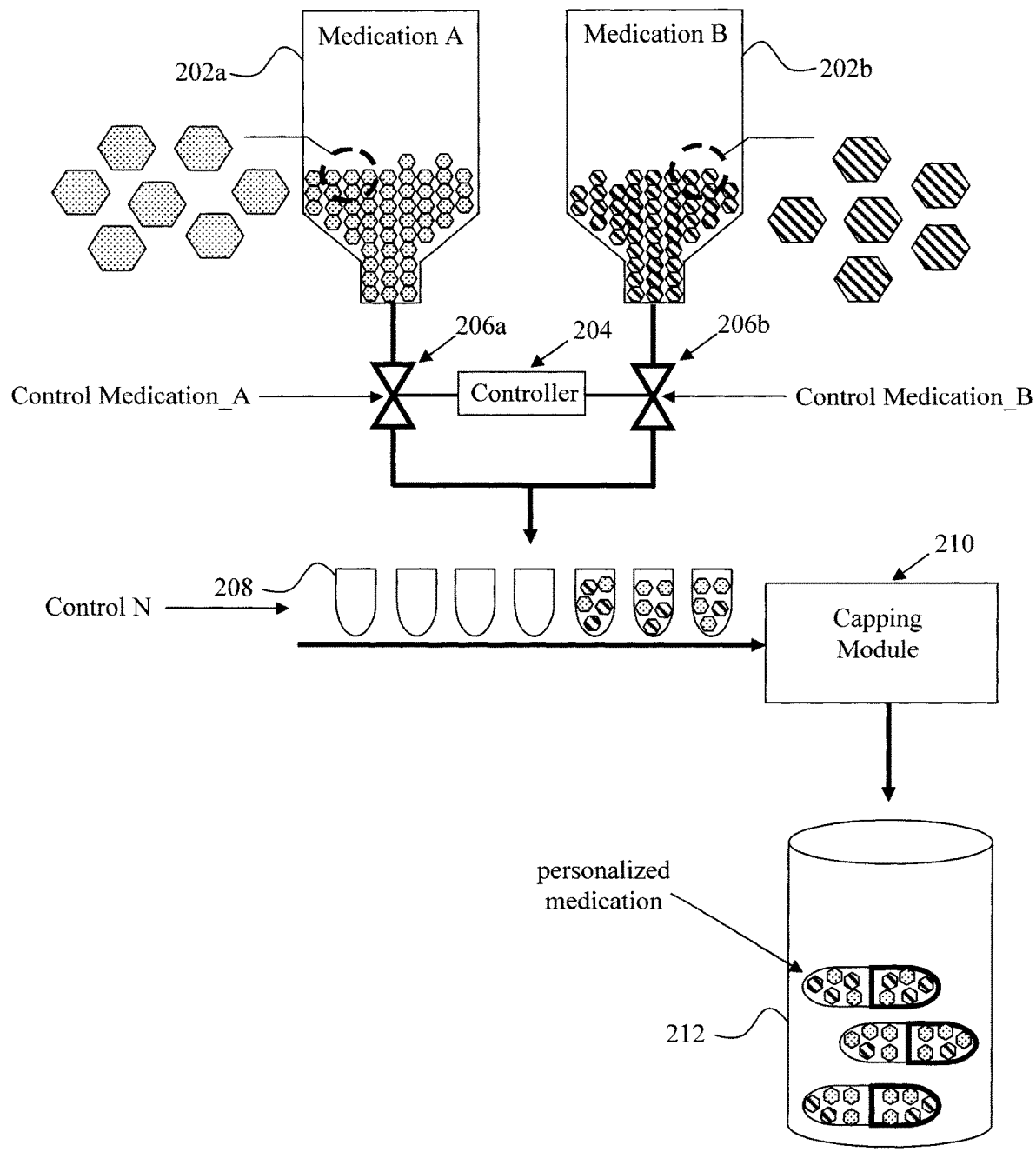
FIG. 2 is a diagram illustrating a Medication Dispenser component of the medication dispenser system according to an embodiment of the present invention.

FIG. 2 is a diagram illustrating an exemplary configuration of the Medication Dispenser component of system 100. As provided above, the Medication Dispenser component dispenses the proper amount of one or more medications based on the dosage determination from the Dosage Calculator. As shown in FIG. 2, the Medication Dispenser component includes the medications individually contained in separate containers 202a, 202b, etc. The individual medications can be placed in the respective containers manually (e.g., by a pharmacist, employee at a supplement distribution center, etc.) from stock supplies or the process can be automated where a loading robot can also be used to fetch and load the needed medications for filling the containers. See, for example, the Robotic Prescription Dispensing Systems available from ScriptPro, Mission, Kans. Each container 202 preferably includes identification features (such as radio frequency ID and/or barcodes) that are read by the controller, so the error of dispensing an incorrect medication is eliminated.

The particular medications are represented generically in the figure as Medication A, Medication B, etc. The use of two medications in the example is merely meant to illustrate the present techniques, and embodiments are anticipated herein wherein the Medication Dispenser component of system 100 includes more containers/medications. Further, the medications in the containers can be in a variety of different forms. For instance, when in solid form the medication in each container is finely granulated (e.g., into a powder) so that a precise amount of the medication can be dispensed. One or more of the containers may contain medications in a liquid form. Precise amounts of a liquid can be easily dispensed. It is possible that medications in different forms (e.g., powders and liquids) might be mixed into a single treatment. For example, some type of medications comes in a suspension form which is basically a liquid with particulates.

A controller 204 receives the dosage data for each of the medications from the Dosage Calculator. The controller 204 is in turn connected to a set of valves 206a, 206b, etc. that each controls the amount of medication that is dispensed from each of the containers. It is noted that there are likely more medications/containers present in the Medication Dispenser component of system 100 than are needed to prepare the treatment. It is through the action of the controller 204 and valves 206, that the particular medications (and their respective amounts) are selected. The use of multiple containers with varying doses can also be implemented herein to further accelerate the dispensing process. By way of example only, in order to dispense a Medication A with a dose of 428 mg, there can be three containers of the same medication. The first container will have granulates each containing 100 mg of Medication A, the second container will hold granulates each containing 10 mg of Medication A, and the third container will hold granulates each containing 1 mg of Medication A. This way four granulates can be dispensed from the first container, two granulates from the second container and eight granulates from the third container. This is likely to be faster and less prone to measurement error if just the third container was used to dispense 428 granulates of 1 mg. The same principle can be applied to liquids.

It is further noted that the dosages required for a particular patient might vary from one treatment to another. For instance, certain treatment regimes require varying the dose of a medication(s) given to a patient over time—such as some antidepressants, medications affecting the adrenergic system, corticosteroids, etc. which require tapering the dosage over time and the patient is given specific treatments to be taken at specific times during the treatment period. Thus the depiction of the individual treatments being dispensed into a common vial (labeled "personalized medication") is merely an example, and embodiments are anticipated herein where the treatments are delineated for the patient such as markings on the treatment (e.g., the capsules may be labeled with "day 1," "day 2," etc.) and/or are arranged in series, such as in a labeled conventional blister packaging. Alternatively (or additionally), capsules may have different colors. They may have different shades for different strength, for example. A user can choose her favorite color from a menu. The system may automatically use different colors or shapes for capsules or tablets containing different medications. The package containing the medication may also have different shapes, colors or textures. Packages may also include Braille script or custom engravings. Capsules may further be packed according to a specific order in a sealed (e.g., with plastic or aluminum foil) tray, where the second dose is located adjunct to the first dose, etc.

The controller 204 sets each of the valves 206 to dispense the requested dose of the medication from each container 202 into a treatment vessel 208. In the example depicted in the figures, the treatment vessel 208 is a capsule. However, the present techniques are more broadly applicable to preparing any types of treatments for which specific dosing is beneficial. Other applications include, but are not limited to, preparing medications given parenterally (e.g., intravenously or intramuscularly), medications applied topically (e.g., in the form of drops, creams, or ointments, etc. Further, the particular vessel can vary depending on the medication/ application. For instance, some medications might be ingested and the release of the medications (e.g., in the stomach, intestines, etc.) may be regulated based on the particular capsule the medication is contained in. The details of time-release techniques for medications are generally known in the art. Thus, depending on the information received from the Patient Information component 102, the Medication Dispenser component 106 might select a particular type of capsule for the medications being dispensed.

In the example shown in FIG. 2, the treatment vessels 208, e.g., capsules, are placed beneath the respective containers 202, and the correct amounts of the respective medications A, B, etc. are dispensed into the vessels 208. This process is coordinated by the controller 204 using the valves 206. For instance, as shown in FIG. 2, the controller 204 controls the dispensing of Medication_A into the vessels 208 via valve 206a, the controller 204 controls the dispensing of Medication_B into the vessels 208 via valve 206b, and so on. The process proceeds in this manner until all of the medications (i.e., N total medications) are dispensed into each of the vessels 208.

A capping module 210 is then used to cap the treatment vessels (e.g., capsules) containing the proper dose(s) of the one or more medications A, B, . . . , N from the containers 202. By way of example only, when the treatments are contained in capsules, the capping module 210 might take a cap from a reservoir of caps (not shown) and place a cap on each of the capsules. Each treatment (e.g., capsule) will now contain all of the medications, in the proper dosages for a patient. Thus, at the prescribed times (e.g., once a day, twice a day, etc. as based on a doctors' prescription, administration instructions for OTC medications and supplements, etc.) the patient can take a single treatment (e.g., a single capsule) to receive the proper dosage of each of the medications. This eliminates the potential for dosage errors and/or for the patient inadvertently forgetting to take a particular medication (especially in the case of multiple medications).

As provided above, the dosage of the medication/medications might vary depending on when they are taken by the patient. For instance, an antibiotic regime might start off with a high dose that tapers off over the treatment period. In that case, it is important for the patient to be able to know which treatment vessel (e.g., capsule) to take at what time. Thus, the capping module 210 may be able to place select caps on select capsules. For example, the caps may be pre-labeled with text such as "Day 1," "Day 2," etc. The capping module 210 may be coordinated with the controller 204 to know which capsule is being filled in the sequence and select the labeled caps in the series accordingly.

The capping module 210 is not specific for capsules, and other treatment vessels can be processed in the same manner described. For instance, vials for containing (e.g., ingestible, injectable, etc.) liquids, containers for creams, ointments, etc. can all be capped via the capping module 210.

Once capped, the personalized medications can then be placed in a vial 212 or other suitable container for the patient. See FIG. 2.

Using the same medication quantity measurement technology, medications can be formulated into a liquid product such as a syrup or an emulsion of variable concentration, such that a fixed, convenient volume unit (e.g., a teaspoon) contains the right amount of medication(s) for the particular patient. Alternatively, the present system may dispense pre-filled syringes or infusion bags with either a fixed volume of liquid formulation or with varying volumes of a fixed concentration liquid formulation that contains one or more doses. In yet another embodiment, a dry form of the medication(s) (e.g., a powder or fine granules) can be packed in a bottle, to which a predetermined amount of liquid (e.g., water) can be added before use to form a syrup or an emulsion. Additionally, the medications can be formulated into infusable liquids, tablets, capsules, caplets, edible forms, gels, creams, ointments, skin patches, drops, syrup, suspensions, or any other suitable forms of delivery.

The present techniques can also be used to dispense liquid or powdered food such as infant formula or supplemental liquid nutrition wherein the generic formula is personalized for a particular patient based on their specific nutritional requirements by adding the required ingredients at the required amount to the generic formula. This applies both to added food supplements (e.g., dietary fiber), minerals, vitamins. It also applies to OTC and prescription medications that can be integrated with a liquid meal. For instance, a personalized nutrition formula may use only specific kinds of amino acids or proteins, fatty acids or triglycerides, or enrich foods with any of these components. For example, a personalized formula may be gluten and lactose free and include only medium-chain triglycerides.

The present techniques can further be used to prepare herbal and homeopathic products, which typically are prescribed in an individualized form and are prepared individually in a pharmacy. Preparations with one or more ingredients can be prepared in custom size or quantity by a manufacturing facility based on prescriptions sent to that facility and distributed (e.g., mailed) to customers.

The present system can further arrange for the delivery of the ordered OTC or nutritional supplement via mail or a pick-up location such as a pharmacy. For some common OTC medication or supplements the Medication Dispenser component may be located at the pharmacy or even at the patient's home. This may allow further flexibility and ad hoc service for customized medication.

Further features anticipated for the present system include, for example, means for printing an individualized code (for example a barcode or a mini/micro matrix barcode quick response (QR) code) on the capsule that can be scanned by a mobile device such as a smart phone. This allows the patient to keep a record of his/her intake of medications, and further reduce the chance of an error, for example taking a medication at the wrong time, or prevent overdosing (if medication was already taken earlier). Reading the bar code can further provide specific instruction such as "take the medication with food," or "avoid driving after taking this medication." Additionally, the capsule size may be too small to print instructions that are readable by eye. The bar code reading by the mobile device may allow large font instruction or a figure on the mobile device display, and more space for detailed instructions. The present system may also permit customized grouping of combined medications—i.e., the system will allow the user to customize how to group medications, for instance, those that need to be taken before eating and those after, those that need to be taken on daily basis vs. those needs to be taken on for a short instance (e.g., antibiotics).

Figure 3:
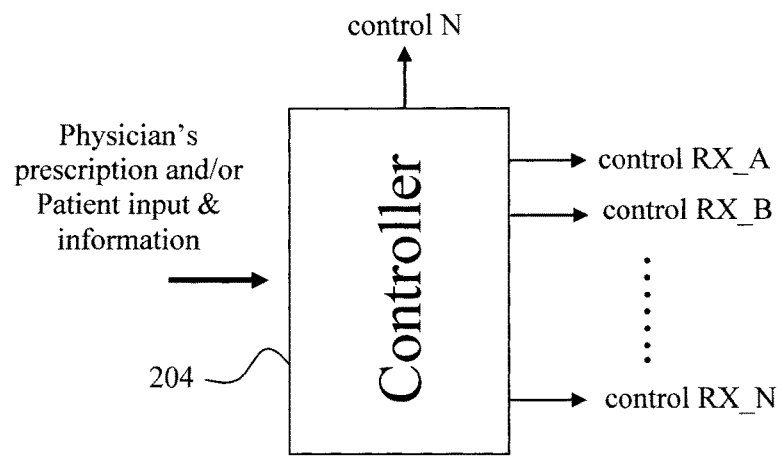
FIG. 3 is a diagram illustrating an exemplary configuration of a controller present in the Medication Dispenser component according to an embodiment of the present invention.

An exemplary configuration of the controller 204 is now described by way of reference to FIG. 3. As shown in FIG. 3, the controller 204 can take as input the dosage data for each medication (obtained in this example via the dosage calculator from a physician's prescription). The prescriptions (abbreviated herein as RX) for medications A, B, . . . , N are designated as RX_A, RX_B, . . . , RX_N, respectively. The controller 204 then controls the amounts of the N medications dispensed into each of the treatment vessels as described above.

As provided above, exact personal dosing of prescription medications is only one exemplary implementation of the present techniques. System 100 can be used for dispensing OTC medications, supplements, cosmetics such as creams or perfumes, etc. based on the information collected by the Patient Information component.

Figure 4:
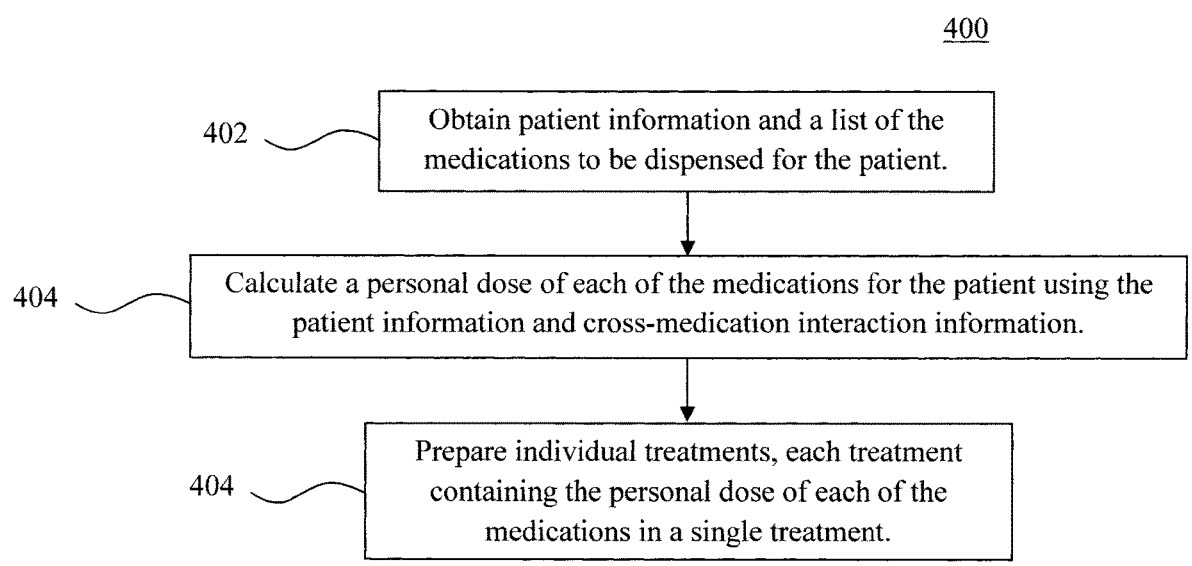
FIG. 4 is a diagram illustrating an exemplary methodology for dispensing medications using, for example, the system of FIG. 1 according to an embodiment of the present invention.

FIG. 4 provides an exemplary methodology 400 for dispensing medications using, for example, system 100. To begin the process, in step 402 patient information (e.g., patient's age, height, weight, gender, use of other medications, metabolism rate, body composition, kidney function, liver function, preferences (e.g., taking medication with or without food, etc.) and a list of the medications to be dispensed for the patient are obtained. This can be performed by the Patient Information component of system 100. As provided above, the patient information can be garnered from a number of different sources. For instance, the patient his/herself might directly provide the necessary information (for instance, via an online or mobile device app, at a kiosk, etc.). The patient might also authorize the system to obtain the patient's medical records. Medical records will contain much of the above-described patient information. Additionally, patient/medication and/or dosage information can be obtained from a physician's prescription. As described above, the present techniques are applicable to a variety of medications including, but not limited to, prescription medications, OTC medications, supplements, etc.

In step 404, a personal dose of each of the medications for the patient is calculated using the patient information. This can be performed by the Dosage Calculator component of system 100. For instance, as provided above, the Dosage Calculator can take the patient information from step 402 and determine the proper dosage for each of the medications. This may involve the age, height, weight, etc. information, medical records data, and/or prescription information, as well as known cross-medication interactions that may affect dosage.

In step 406, individual treatments are prepared, each treatment containing the personal dose of each of the medications in a single treatment. That way the patient need only take a single treatment (at the prescribed time(s)) to receive the proper dosage of each medication contained in the treatment. The treatments might be packaged in a pill/capsule form, in a vial, in an ingestible/injectable liquid, etc. As provided above, when the dosage of the treatments vary (for example based on when they are to be taken—such as with a tapered course of antibiotics) then each treatment might be individually labeled and/or packaged to indicate the proper series of treatments (e.g., labeling the treatments "Day 1," "Day 2," etc.).

Figure 5:
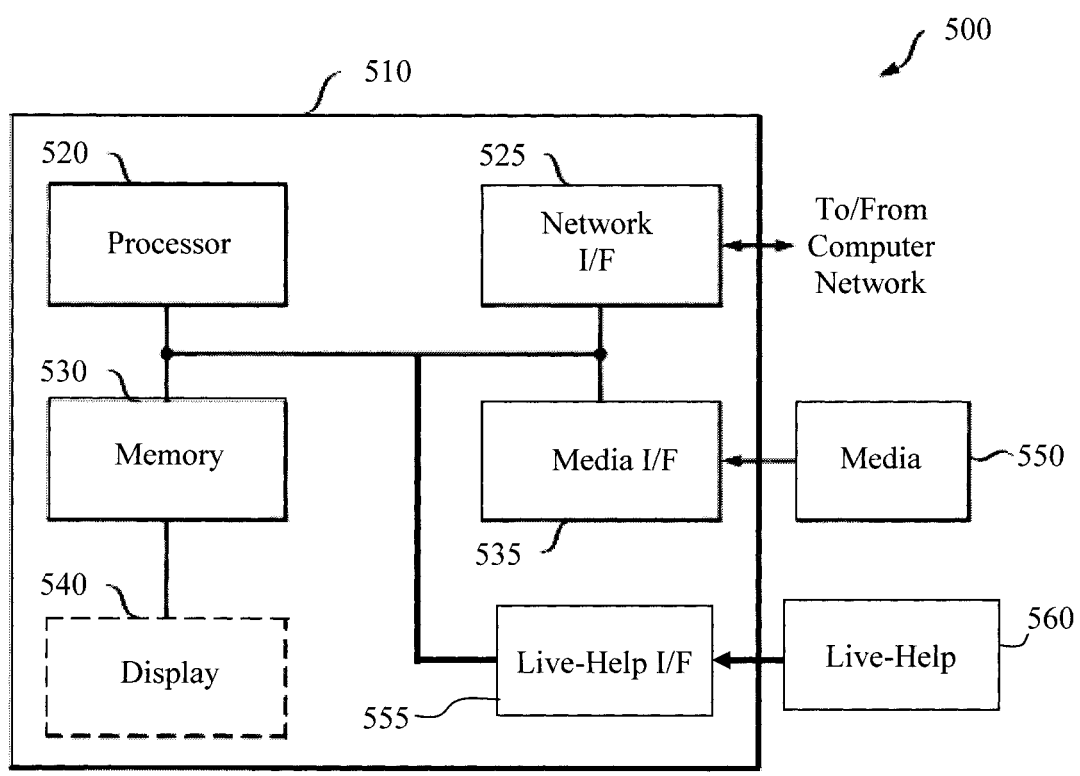
FIG. 5 is a diagram of an exemplary apparatus for implementing one or more of the methodologies presented herein according to an embodiment of the present invention.

Turning now to FIG. 5, a block diagram is shown of an apparatus 500 for implementing one or more of the methodologies presented herein. By way of example only, apparatus 500 can be configured to perform one or more of the steps of methodology 400 of FIG. 4.

Apparatus 500 includes a computer system 510 and removable media 550. Computer system 510 includes a processor device 520, a network interface 525, a memory 530, a media interface 535, a live-help interface 555, and an optional display 540. Network interface 525 allows computer system 510 to connect to a network, while media interface 535 allows computer system 510 to interact with media, such as a hard drive or removable media 550, and live-help interface 555 allows computer system 510 to interact with a Live Person 560 (e.g., a nurse, doctor, dietician, or other practitioner on a help line). This live help interface could be implemented using a messenger application over the network or a phone line.

Processor device 520 can be configured to implement the methods, steps, and functions disclosed herein. The memory 530 could be distributed or local and the processor device 520 could be distributed or singular. The memory 530 could be implemented as an electrical, magnetic or optical memory, or any combination of these or other types of storage devices. Moreover, the term "memory" should be construed broadly enough to encompass any information able to be read from, or written to, an address in the addressable space accessed by processor device 520. With this definition, information on a network, accessible through network interface 525, is still within memory 530 because the processor device 520 can retrieve the information from the network. It should be noted that each distributed processor that makes up processor device 520 generally contains its own addressable memory space. It should also be noted that some or all of computer system 510 can be incorporated into an application-specific or general-use integrated circuit.

Optional display 540 is any type of display suitable for interacting with a human user of apparatus 500. Generally, display 540 is a computer monitor or other similar display.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method for dispensing medications, the method comprising the steps of:
    obtaining patient information and a list of the medications for the patient;
    calculating a personal dose of each of the medications for the patient by applying the patient information to manufacturer-specified dosage specifications and cross-medication interaction information; and
    preparing treatments, wherein each of the treatments contains the personal dose of each of a plurality of the medications for the patient combined in a single treatment, and wherein the step of preparing the treatments comprises dispensing the personal dose of the plurality of the medications into a single vessel as the single treatment such that the patient need only take the single treatment contained in the vessel to receive the personal dose of each of the plurality of the medications the patient is taking, wherein the step of preparing the treatments further comprises the step of varying the personal dose of at least one of the medications from one treatment to another, wherein at least one of the medications is dispensed from multiple containers containing different doses of a same medication, and wherein the step of preparing the treatments further comprises dispensing a different amount of the same medication from each of the multiple containers at the different doses which, when combined in the vessel, provides the personal dose of at least one of the medications, and wherein the treatments comprise patient-specified combinations of the medications and an associated color coding chosen by the patient, whereby the patient customizes how to group the medications during the preparing of the treatments and assigns a color, chosen by the patient from a menu, to the vessel into which the treatments are dispensed.

2. The method of claim 1, wherein the patient information comprises at least one of: age, height, weight, gender, and use of other medications.

3. The method of claim 1, wherein the patient information is obtained directly from the patient.

4. The method of claim 1, wherein the patient information is obtained from medical records.

5. The method of claim 1, wherein the medications comprise over the counter medications or supplements.

6. The method of claim 1, wherein the medications comprise prescription medications.

7. The method of claim 6, wherein the patient information comprises dosage information provided on prescriptions for the medications.

8. The method of claim 1, wherein the medications comprise at least one of: liquid products, powders, infusable liquids, tablets, capsules, caplets, edible forms, gels, creams, ointments, skin patches, drops, syrup, and suspension.

9. The method of claim 1, wherein the step of preparing the treatments comprises the step of:
    placing each of the treatments in a separate vessel.

10. The method of claim 1, wherein the vessel comprises at least one of a capsule, a tablet, and a vial.

11. The method of claim 1, further comprising the step of:
    capping the vessel.

12. The method of claim 1, wherein at least one of the plurality of the medications comprises a powder, and at least another one of the plurality of the medications comprises a liquid, and wherein the powder and the liquid are combined in the single treatment.

13. The method of claim 1, further comprising the step of:
    printing an individualized code on the vessel that is scannable by a smart phone of the patient, wherein the individualized code is selected from the group consisting of: a barcode, and a matrix barcode, and wherein the individualized code, when scanned by the smart phone, provides specific instructions for taking the treatments.

14. The method of claim 1, wherein the multiple containers contain granulates of the same medication at the different doses, and wherein the step of preparing the treatments further comprises dispensing a different number of the granulates from each of the multiple containers at the different doses which, when combined in the vessel, provides the personal dose of the at least one medication.

15. The method of claim 1, wherein the patient-specified combinations of the medications comprise a grouping of the medications taken before eating, and another grouping of the medications taken after eating.

16. A system for dispensing medications, comprising:
a patient information component for obtaining patient information and a list of the medications for the patient;
a dosage calculator component for calculating a personal dose of each of the medications for the patient by applying the patient information to manufacturer-specified dosage specifications and cross-medication interaction information; and
a medication dispenser component for preparing treatments, wherein each of the treatments contains the personal dose of each of a plurality of the medications for the patient combined in a single treatment, and wherein the preparing of the treatments comprises dispensing the personal dose of the plurality of the medications into a single vessel as the single treatment such that the patient need only take the single treatment contained in the vessel to receive the personal dose of each of the plurality of the medications the patient is taking, wherein the preparing of the treatments further comprises varying the personal dose of at least one of the medications from one treatment to another, wherein the medication dispenser component comprises multiple containers containing different doses of a same medication, and wherein the preparing of the treatments further comprises dispensing a different amount of the same medication from each of the multiple containers at the different doses which, when combined in the vessel, provides the personal dose of at least one of the medications, and wherein the treatments comprise patient-specified combinations of the medications and an associated color coding chosen by the patient, whereby the patient customizes how to group the medications during the preparing of the treatments and assigns a color, chosen by the patient from a menu, to the vessel into which the treatments are dispensed.

17. The system of claim 16, wherein the medication dispenser component is configured to place each of the treatments in a separate vessel, the system further comprising a capping module for capping the vessel.

18. The system of claim 16, wherein the vessel comprises at least one of a capsule, a tablet, and a vial.

19. The system of claim 16, wherein the medications comprise at least one of: liquid products, powders, edible forms, gels, creams, ointments, skin patches, drops, syrup, and suspension.

* * * * *